(12) United States Patent
McDonald

(10) Patent No.: US 6,248,123 B1
(45) Date of Patent: Jun. 19, 2001

(54) FORCEPS WITH SLIDER ADJUSTMENT

(75) Inventor: Henry H. McDonald, Rancho Mirage, CA (US)

(73) Assignee: Surgical Concepts, Inc., Newport Beach, CA (US)

( * ) Notice: Subject to any disclaimer, the term of this patent is extended or adjusted under 35 U.S.C. 154(b) by 0 days.

(21) Appl. No.: 09/480,938

(22) Filed: Jan. 11, 2000

(51) Int. Cl.$^7$ ................ A61B 17/50; A61F 9/00
(52) U.S. Cl. .......................... 606/210; 606/107
(58) Field of Search ............... 606/205, 206, 606/208, 210, 133, 151, 157, 158; D28/28; D24/143; 294/99.2; 433/159; 451/389; 81/7, 308, 303, 307, 312, 318; 29/243.56; 24/455, 461, 492, 513, 515, 568

(56) References Cited

U.S. PATENT DOCUMENTS

| | | | |
|---|---|---|---|
| 125,311 | * 4/1872 | Lucas | 24/515 |
| 581,810 | * 5/1897 | Clarkson | 294/99.2 |
| 775,034 | * 11/1904 | Grape | 24/502 |
| 3,409,954 | * 11/1968 | Schneider | 294/99.32 |
| 4,324,248 | * 4/1982 | Perlin | 606/158 |
| 4,337,774 | * 7/1982 | Perlin | 606/158 |
| 4,991,267 | * 2/1991 | Apperson et al. | 24/515 |
| 5,732,921 | * 3/1998 | Lemire | 24/515 |
| 5,776,139 | 7/1998 | McDonald . | |

* cited by examiner

Primary Examiner—Henry J. Recla
Assistant Examiner—(Jackie) Tan-Wen Tan-uyen T. Ho
(74) Attorney, Agent, or Firm—William W. Haefliger

(57) ABSTRACT

Apparatus used for manipulation of a gripped element employed in surgery, which includes two elongated lever arms, each of which has a distal first zone, and a second zone or zones rearward of distal first zone, and a handle from which the arms extend forwardly; the arms supported so that first distal zones are yieldably urged toward one another by the arms to hold the gripped element therebetween; and a pusher movable between the arms to pivot one arm relative to the other arm in response to controllable force exertion acting on the pusher, as from a location outside the arms, thereby to cause the first zones to relatively move, enabling gripping or release of the element.

25 Claims, 2 Drawing Sheets

FORCEPS WITH SLIDER ADJUSTMENT

BACKGROUND OF THE INVENTION

This invention relates generally to forceps type apparatus with sensitive adjustment, and more specifically, concerns improvements in surgical forceps type instruments responsive to finger pressure.

There is continual need for improvements in forceps adjustability and sensitivity to manual adjustment; and in particular for improvements as are described herein, to provide unusual advantages as will appear.

SUMMARY OF THE INVENTION

It is a major object of the invention to provide improved instrumentation meeting the above-described need.

Basically, the herein-described apparatus is used for manipulation of a gripped element employed as for example in surgery, which includes:

a) two elongated lever arms, each of which has a distal first zone, and a second zone or zones rearward of the distal first zone, and a handle from which the arms extend forwardly, b) the arms supported so that the first distal zones are yieldably urged toward one another by the arms to hold the gripped element therebetween, c) a pusher movable between the arms to pivot one arm relative to the other arm in response to controllable force exertion to the pusher, from a location outside the arms, thereby to cause the first zones to relatively move, enabling gripping or release of the element.

As will be seen, the gripped element may be positioned between the forceps arm first distal zones, to be released or gripped in response to arm pivoting.

Another object is to provide a slider slidable externally of such arms, to operate a pusher having camming engagement with at least one of the arms, at the second zone or zones. The pusher may be carried or positioned between the arms, for such camming engagement, as for example with slide camming surfaces of both arms, in response to sliding movement of the slider along one of the arms. A connector may be used to interconnect the slider and pusher, and to pass through one of the arms.

A further object is to provide a space between the arms, to receive the pusher inwardly of the slider, for adjusting the spreading of the arms, in infinitely and sensitively adjustable manner as the slider is displaced.

An additional object is to provide a method of manipulating an element to be gripped for use in surgery, which includes a) providing two elongated lever arms, each of which has a distal first zone, and a second zone or zones rearward of the distal first zone, and providing a handle from which the arms extend forwardly, b) the arms supported so that the first distal zones are yieldably urged toward one another by the arms to hold the gripped element therebetween, c) at least one of the arm second zones configured to pivot relative to the other arm in response to controllable force exertion acting between the arms, d) and from the exterior of the arms, exerting controlled force acting between the arms to cause at least one arm to pivot relative to the other arm for enabling gripping or release of the element by the first distal zones, As referred to, an arm pusher may be provided via which such controllable force is applicable to the arms to cause at least one arm to pivot relative to the other arm; and the pusher may be positioned between the second zones of the two arms to have sliding engagement with the arms, in response to finger pressure on a slider located exteriorly of the arms.

A yet further object is to exert controllable force on the pusher, via the slider, to cause the pusher to controllably and relatively spread the arms in response to sliding engagement therewith, and with space provided between the arms to receive the user's finger to operate the pusher. The method may also include accurate release of the element, by exerting highly sensitively adjustable force on the slider.

A further object is to provide for pusher camming engagement with at least one of the arms so as to provide mechanical advantage whereby pusher displacement by an amount $d_1$ exceeds relative spreading of the two arm distal zones by an amount $d_2$, expressed as $d_1 > d_2$.

These and other objects and advantages of the invention, as well as the details of an illustrative embodiment, will be more fully understood from the following specification and drawings, in which:

DRAWING DESCRIPTION

DETAILED DESCRIPTION

Figure 1:
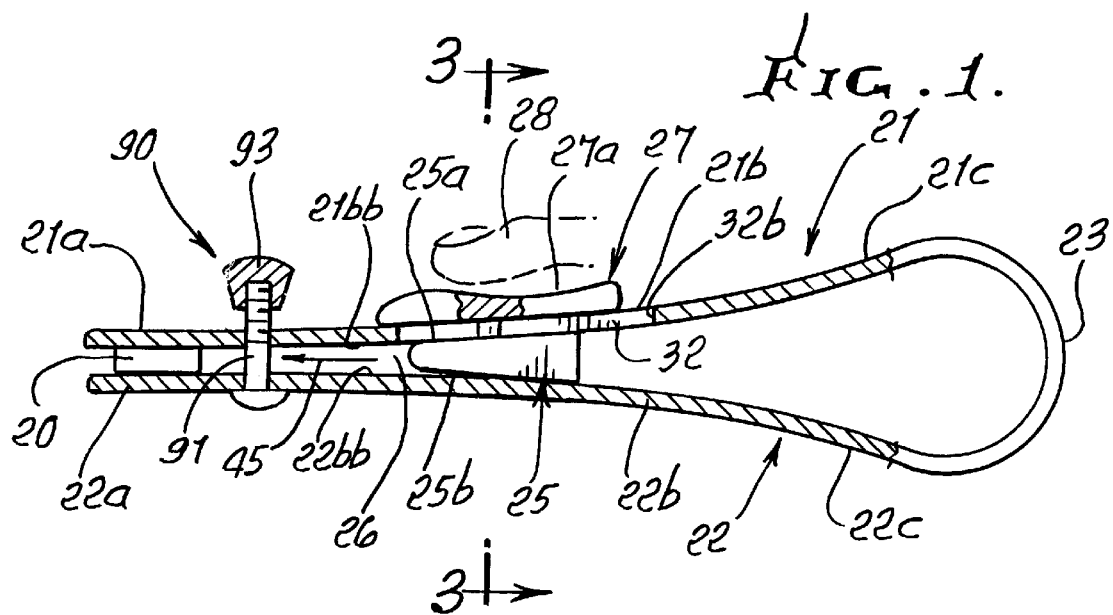
FIG. 1 is a side elevation showing a preferred embodiment, and an element or object gripped by the device.
Figure 2:
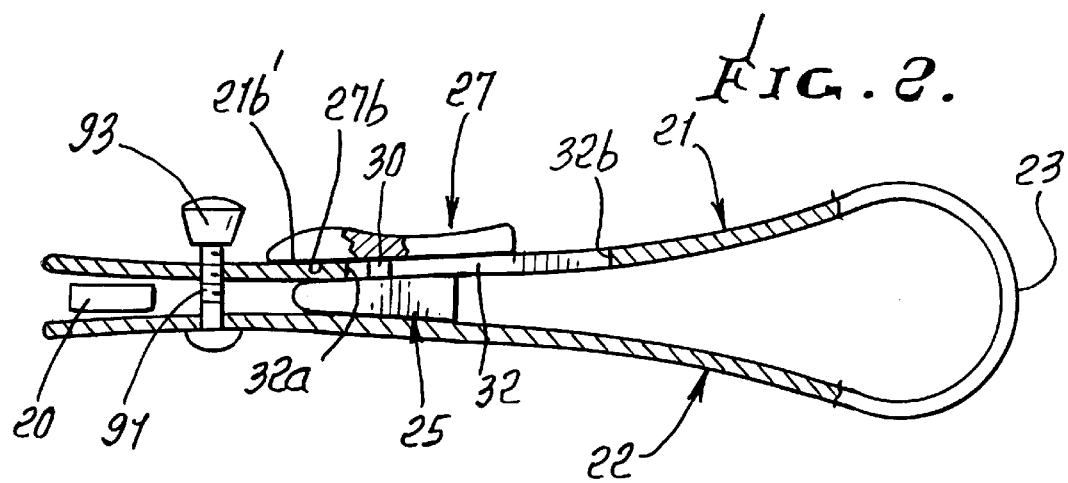
FIG. 2 is a view like FIG. 1 but showing release of the object in response to slider and pusher forward movement.
Figure 3:
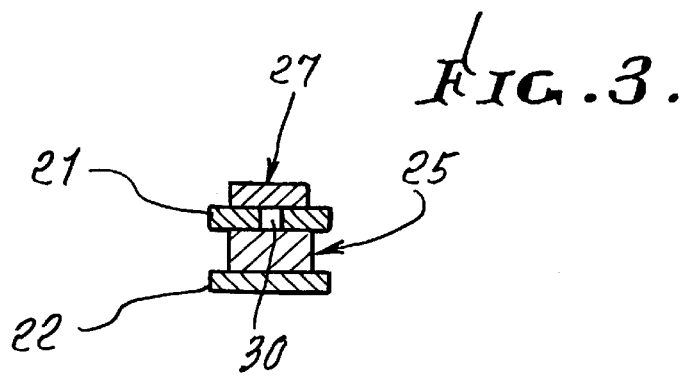
FIG. 3 is a section taken on lines 3—3 of FIG. 1.

In FIGS. 1 and 2, a gripped element employed in surgery is shown at 20. It is gripped between the distal ends or first zones 21a and 22a of two elongated arms 21 and 22, respectively. Element 20 may, for example be an artificial lens to be inserted into the eye.

The two arms have second or intermediate zones 21b and 22b rearward of and spaced from the two distal zones; and they have handles 21c and 22c rearward of zones 21b and 22b. The two handles are typically coupled together rearwardly of zones 21b and 22b, as at 23. Distal zones 21a and 22a are or may be yieldably urged toward one another by the two arms to lightly, but firmly, grip the element 20 therebetween, for manipulation. As shown, in one example, the arms are, or may be, interconnected by bowed spring segment 23 at the rearward extents of the two handles.

In accordance with the invention, a pusher is movable between the arms to pivot one arm relative to the other arm in response to controllable force exertion on the pusher, from a location outside said arms, and outside the space 26 between the arms, thereby to cause the arm first zones to relatively move, enabling gripping or release of said element. One such pusher appears at 25, in the space 26 between the arm zones 21b and 22b, and is movable in forward direction indicated by arrow 45 to effect controlled wedging apart of the arms, including distal zones 21a and 22a. To this end, the pusher may typically have wedge shape, between its wedging surfaces 25a and 25b that exert wedging force transmitted to arm inner surfaces 21bb and 22bb.

Further, a slider is located outwardly of said arms and operatively connected to the pusher to transmit controllable force exertion to the pusher. One such slider is shown at 27, externally of the arms, to enable its controlled manual forward sliding in direction 45, as by thumb or finger pressure against surface 27a presented outwardly. That surface has shallow concavity to conform to the convex shape of the user's thumb or finger 28. The slider has an inner surface 27b that slides along the outer surface 21b' of the arm zone 21b, as shown.

Operative connection of the slider to the pusher is preferably provided by a connector interconnecting the slider and pusher. See for example the connector 30 extending between the slider and pusher, to position these components in the positions shown, for operation as described. Thus, the connector allows the pusher to position the slider adjacent outer surface 21b', to slide therealong, and allows the slider to position the pusher to wedge apart the arms to selected extent as the slider is moved forwardly, toward the distal zones. An aperture is provided through the arm 21, as by slot at 32, and may be elongated to allow forward and rearward movement of the connector that extends through the aperture. The ends of the aperture or slot at 32a and 32b limit longitudinal movement of the connector, and thereby limit movement of the slider and pusher.

In operation, the pusher is provided to have wedging camming engagement with at least one of the arms to thereby provide mechanical advantage whereby pusher displacement by an amount $d_1$, exceeds relative spreading of the two arm distal zones by an amount $d_2$, expressed as $d_1 > d_2$. Very accurate control of the element 20 is thereby achieved, as for example where $d_1$ is less than ½ $d_2$, i.e. $d_1$ may be ⅛ inch when $d_2$ (slider movement) is ½ inch, for example. The method includes exerting controllable force on the slider to cause the pusher to controllably and relatively spread the arms in response to sliding engagement therewith.

Enhanced gripping of the element 20 is achievable by the mechanical advantage of slider and pusher back and forth movement, over the movement of the distal zones toward and away from one another. It will also be noted that the pusher is retained in selected forwardly advanced, arm wedging position, by friction forces exerted by the pusher surfaces 25a and 25b on the arm inner surfaces 21bb and 22bb.

Also provided is an adjustable holder operatively connected with the arms to hold them in selected adjusted spacing at said first distal zones. As shown, the representative holder 90 includes a stem 91 extending between the arms near the distal zones 21a and 22a. A nut 93 thread connected to the stem may be tightened to bear on arm 21 and thereby to hold the arms at selected separation.

Figure 4:
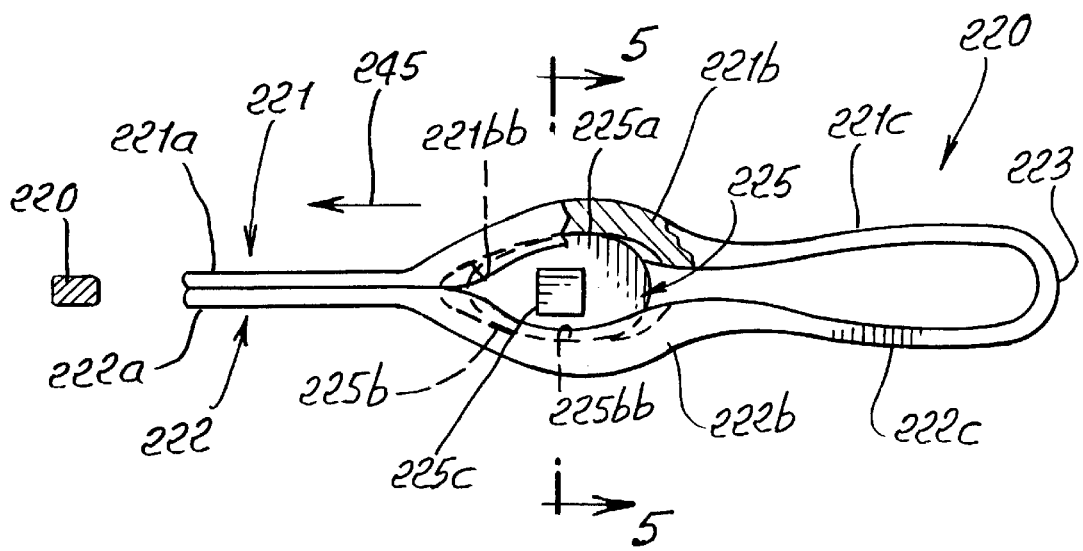
FIG. 4 is a view like FIG. 1, showing a modification.
Figure 5:
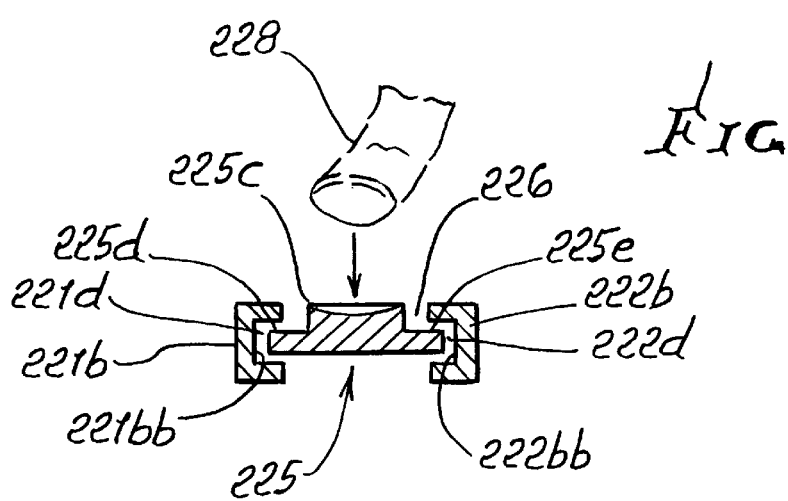
FIG. 5 is an enlarged section taken on lines 5—5 of FIG. 4.

In FIGS. 4 and 5, showing in top view a modified device, an element to be employed in surgery is shown at 220. It is to be gripped between the distal ends or first zones 221a and 222a of two elongated arms 221 and 222, respectively. Element 220 may, for example be an artificial lens to be inserted into the eye.

The two arms have second or intermediate zones 221b and 222b rearward of and spaced from the two distal zones; and they have handles 221c and 222c rearward of zones 221b and 222b. The two handles are typically coupled together rearwardly of zones 221b and 222b, as at 223. Distal zones 221a and 222a may be spread apart by the arms, and yieldably urged toward one another by the two arms to lightly, but firmly, grip the element 220 therebetween, for manipulation. As shown, in one example, the arms are, or may be, interconnected by bowed spring Segment 223 at the rearward extents of the two handles.

A pusher is movable between the arms to pivot one arm relative to the other arm in response to controllable force exertion on the pusher, from a location generally intermediate the arms, thereby to cause the arm first zones to relatively move, enabling gripping or release of the element 220. One such pusher appears at 225 in the space 226 between the arm zones 221b and 222b, and is movable in forward direction indicated by arrow 245 to effect controlled wedging apart of the arms, including distal zones 221a and 222a. To this end, the pusher may typically have wedge shape, between its tapering wedging surfaces 225a and 225b that exert wedging force transmitted to arm inner surfaces 221bb and 222bb.

Further, the pusher has a projection 225c located intermediate the arms, but accessible via space 226, and is finger manipulable to transmit controllable force exertion to the pusher 225, such force exerted from a location outside arms 221 and 222. Projection 225c may have the form of a button engagable by thumb or finger pressure against its top surface presented outwardly. That surface may be dished to have shallow concavity to conform to the convex surface shape of the user's thumb or finger 228.

Operative connection of the pusher 225 to the arms is preferably provided as by guided interconnection of the arms and pusher. See for example the pusher lateral extents 225d and 225e guided in arm inner grooves or slots 221d and 222d to guidingly position the pusher for forward and rearward sliding operation, as described. Thus, the arm connections allow the pusher to slide therealong, and to wedge apart the arms to selected extent as the pusher is moved forwardly, toward the distal zones.

In operation, the pusher is provided to have wedging camming engagement with at least one of the arms to thereby provide mechanical advantage whereby pusher displacement by an amount $d_1$, exceeds relative spreading of the two arm distal zones by an amount $d_2$, expressed as $d_1 > d_2$. Very accurate control of the element 20 is thereby achieved, as for example where $d_2$ is less that ¼ $d_2$, i.e. $d_1$ may be ⅛ inch when $d_2$ (slider movement) is ½ inch, for example. The method includes exerting controllable force on the button 225c to cause the pusher to controllably and relatively spread the arms in response to sliding engagement therewith.

Enhanced gripping of the element 220 is achievable by the mechanical advantage of pusher back and forth movement over the movement of the distal zones toward and away from one another. The device of FIGS. 4 and 5 may be considered as preferred.

I claim:

1. Apparatus used for manipulation of a gripped element employed in surgery, which includes:

a) two elongated lever arms, each of which has an inner surface, an outer surface, a distal first zone, and a second zone or zones rearward of said distal first zone, and a handle from which the arms extend forwardly, b) said arms being biased by a looping arm extension such that said first distal zones are yieldably urged toward one another to hold the gripped element therebetween, c) a generally wedge shaped pusher slidable between said inner surfaces of said arms to pivot one arm relative to the other arm in response to controllable force exertion to the pusher, from a location proximate said outer surface of at least one of said arms, thereby to cause said first zones to relatively move toward or away from each other, enabling gripping or release of said element.

2. The apparatus of claim 1 including said element positioned between and gripped by said arm first zones.

3. The apparatus of claim 1 including a slider located outwardly of said arms and operatively connected to the pusher to transmit said controllable force exertion to the pusher.

4. The apparatus of claim 3 wherein said slider is located adjacent one of said arms to be slidable therealong.

5. The apparatus of claim 4 including a connector interconnecting said slider and pusher.

6. The combination of claim 5 wherein the pusher is provided to have wedging camming engagement with at least one of the arms to thereby provide mechanical advantage whereby pusher displacement by an amount $d_1$, exceeds relative spreading of the two arm distal zones by an amount $d_2$, expressed as $d_1 > d_2$.

7. The apparatus of claim 5 including an aperture in said one arm through which said connector extends.

8. The apparatus of claim 1 wherein said pusher has wedge surfaces to wedge between said arms as the pusher is moved forwardly toward said distal zones.

9. The apparatus of claim 4 wherein said pusher has wedge surfaces to wedge between said arms as the pusher is moved forwardly toward said distal zones.

10. The combination of claim 1 wherein said pusher is located between said second zones.

11. The combination of claim 10 wherein the arm second zones are located to provide a space therebetween to receive the pusher.

12. The apparatus of claim 1 including an adjustable holder operatively connected with the arms to hold them in selected adjusted spacing at said first distal zones.

13. The apparatus of claim 1 including a projection on the pusher and presented to receive said controllable force exertion.

14. The apparatus of claim 13 wherein said pusher has tongue and groove slidingly guided interconnection with at least one of said arms.

15. The apparatus of claim 13 wherein said pusher has lateral extents having tongue and groove slidingly guided interconnection with said arms, respectively.

16. The method of manipulating an element to be gripped for use in surgery, which includes a) providing two elongated lever arms, each of which has an inner surface an outer surface, a distal first zone, and a second zone or zones rearward of said distal first zone, and providing a handle from which said arms extend forwardly, b) said arms being biased by a looping arm extension such that said first distal zones are yieldably urged toward one another to hold the gripped element therebetween, c) at least one of said arm second zones configured to pivot relative to the other arm in response to controllable force exertion acting between the arms, there being a generally wedge shaped pusher slidable between said inner surfaces of said arms to pivot one arm relative to the other arm in response to controllable force exertion to the pusher, d) and, from a location proximate said outer surface of at least one of the arms exerting controlled force to the pusher to cause said at least one arm to pivot relative to the other arm for enabling gripping or release of said element by said first distal zones.

17. The method of claim 16 including providing a slider positioned to slide along one of said arms and to transmit said force to said pusher.

18. The method of claim 17 including providing interconnection between the slider and pusher.

19. The method of claim 17 including exerting said controllable force on said slider to cause the pusher to controllably and relatively spread said arms in response to sliding engagement therewith.

20. The method of claim 16 including providing said element in a gripped position between said first distal zones.

21. The method of claim 20 wherein said element is provided in the form of an artificial lens.

22. The method of claim 16 including providing a projection on the pusher presented to receive said controllable force exertion.

23. The method of claim 22 including providing a tongue and groove slidingly guided interconnection between said pusher and at least one of said arms.

24. The method of claim 22 including providing pusher lateral extents having tongue and groove slidingly guided interconnections with said arms.

25. The method of claim 22 including locating said projection generally intermediate said arm second zones.

* * * * *